United States Patent [19]

Khoshdel et al.

[11] Patent Number: 5,372,804
[45] Date of Patent: Dec. 13, 1994

[54] COSMETIC COMPOSITION COMPRISING SUNSCREEN CONTAINING MICROLATEX PARTICLES

[75] Inventors: Ezat Khoshdel, South Wirral; Gerald J. O'Shea, Heswall; Michael J. Parkington, West Kirby, all of United Kingdom

[73] Assignee: Chesebrough-Pond's USA Co., Division of Conopco, Inc., Greenwich, Conn.

[21] Appl. No.: 71,278

[22] Filed: Jun. 2, 1993

[30] Foreign Application Priority Data

Jun. 3, 1992 [GB] United Kingdom ............... 9211708

[51] Int. Cl.⁵ .................. A61K 6/00; A61K 7/42
[52] U.S. Cl. ............................. 424/59; 424/401
[58] Field of Search ............................ 424/401, 59

[56] References Cited

U.S. PATENT DOCUMENTS

| | | | |
|---|---|---|---|
| 4,710,374 | 12/1987 | Grollier et al. | 424/61 |
| 4,753,793 | 6/1988 | Walton | 424/70 |
| 4,798,721 | 1/1989 | Yahazi et al. | 424/71 |
| 4,985,239 | 1/1991 | Yahagi et al. | 424/70 |
| 5,219,561 | 6/1993 | Gagnebin et al. | 424/401 |
| 5,224,598 | 9/1953 | Merrifield et al. | 424/70 |

FOREIGN PATENT DOCUMENTS

| | | | |
|---|---|---|---|
| 0306236 | 3/1989 | European Pat. Off. | |
| 60-224609 | 11/1985 | Japan | 424/401 |

Primary Examiner—Thurman K. Page
Assistant Examiner—Peter F. Kulkosky
Attorney, Agent, or Firm—Rimma Mitelman

[57] ABSTRACT

Improved deposition of a cosmetic agent, e.g. a sunscreen, from a cosmetic composition such as a hair or body shampoo is achieved by incorporating the cosmetic agent in the composition in combination with, e.g. carried on the surface of or within pores of, latex particles of a polymeric material having a particle size of less than about 1 micron.

14 Claims, No Drawings

COSMETIC COMPOSITION COMPRISING SUNSCREEN CONTAINING MICROLATEX PARTICLES

FIELD OF THE INVENTION

The present invention relates to cosmetic compositions, more particularly to cosmetic compositions which include a cosmetic agent to be deposited onto the hair or the skin. Such cosmetic compositions include compositions for washing hair or skin, such as hair shampoos, conditioners, body shampoos, shower gels, facial washing compositions and bath foams.

BACKGROUND OF THE INVENTION AND PRIOR ART

Difficulties arise in achieving effective deposition of cosmetic agents onto skin or hair when the cosmetic agent is delivered by means of incorporation into rinse-off compositions, typically hair and body shampoos, conditioners and the like. Frequently, cosmetic agents, particularly those which are water- and/or surfactant-soluble or -solubilizable, are preferentially rinsed away from the intended site of deposition, rather than being deposited thereat.

Conventional rinse-off compositions therefore have limited efficacy as vehicles for deposition of cosmetic agents and also lead to non-cost-effective use of and waste of cosmetic raw materials.

Water- and/or surfactant-insoluble or -insolubilizable cosmetic agents, on the other hand, also face problems, because their insolubility makes it difficult to achieve stable incorporation at the desired levels, yet giving an adequate degree of deposition of the cosmetic agent from the composition at the intended site.

Cosmetic agents which are soluble or solubilizable in only one of water and surfactant share all of the above mentioned problems, but to intermediate degrees.

It is an object of the present invention to ameliorate the aforementioned disadvantages and to facilitate and/or enhance deposition of cosmetic agents from cosmetic compositions, particularly rinse-off compositions.

One system by which deposition of cosmetic agents from rinse-off cosmetic compositions may be enhanced is disclosed in our co-pending United Kingdom patent application No 9200764.0, in which there is disclosed a rinse-off cleansing composition including one or more surfactant-soluble cosmetic agents, e.g. a sunscreen oil, for deposition onto hair or skin, the composition comprising a stable emulsion having a continuous phase comprising one or more surfactants and an internal phase comprising one or more oil materials, e.g. a silicone oil, wherein the internal oil phase contains the said one or more surfactant-soluble cosmetic agents.

In a different field, for the purpose of topically administering, especially with controlled release, a variety of cosmetically or pharmaceutically active agents, porous microparticles of a polymeric material in which the active agent is impregnated have been utilized as a carrier. Such a system is described for example in EP-A-0306236. Here the disclosed microparticles have a preferred particle size of between 1 and 100 microns, in order to give the compositions in which the microparticles are incorporated aesthetic appeal, particularly smooth feel to the touch. However, the technology relied upon for this type of delivery system tends to be expensive and involves the use of organic solvents, which make the technology environmentally unfriendly and may present safety problems.

During our investigations into the possibility of utilizing particulate polymeric materials as carriers for cosmetic agents to be deposited onto skin or hair from rinse-off cosmetic compositions, it was found that the types of system described in EP-A-0306236 are technically unsuitable, firstly because the disclosed cross-linked polymers are poor film formers and are thus difficult to deposit effectively onto hair or skin, and secondly because the described polymer particles give rise to cosmetic compositions which are not aesthetically pleasing, e.g. they are cloudy.

Also disclosed in the art is the use of certain polymer lattices in combination with cationic polymers for treating the hair, skin or nails, for example as disclosed in U.S. Pat. No. 4,710,374 (corresponding to GB-A-2114580). Here the latex is an anionic latex and when used in combination with a variety of cationic polymers which condition the hair, imparts properties of liveliness, volume, stiffness and hold of the hair which persist for a longer period of time compared with that obtained with known anionic polymers instead of the anionic latices.

The application of hair setting or styling polymers to hair for such cosmetic purposes by way of deposition from cosmetic compositions comprising such polymers in the form of micro-particle latices is also known from U.S. Pat. No. 4,798,721, U.S. Pat. No. 4,985,239 and U.S. Pat. No. 4,753,793. In these references, however, the aim is to apply to the hair the polymer itself for the benefit it imparts and there is no disclosure or teaching of any association between the polymer latex particles and any additional cosmetic substances which may be present in the disclosed compositions.

SUMMARY OF THE INVENTION

We have now found that polymer latices can be used to good effect in aesthetically pleasing cosmetic compositions to give good deposition of a variety of cosmetic agents onto hair or skin, particularly when the polymer latex particles are of sub-micron particle size. We have found that such systems give significantly enhanced deposition of cosmetic agents compared with prior art cosmetic compositions which rely on the conventional deposition technology known in the art and which do not include such sub-micron polymer latex particles.

Accordingly, in a first aspect the present invention provides a cosmetic composition comprising:
 (a) at least one cosmetic agent for deposition onto hair or skin; and
 (b) as a carrier for the cosmetic agent or agents, latex particles of a polymer material having a particle size of less than about 1 micron;
wherein the at least one cosmetic agent is carried in or on the polymer latex particles so as to be deposited onto hair or skin when the composition is applied thereto.

In another aspect, the invention provides a method of facilitating and/or enhancing deposition of at least one cosmetic agent from a cosmetic composition, comprising providing the cosmetic agent or agents in combination with a carrier therefor, the carrier comprising latex particles of a polymer material having a particle size of less than about 1 micron and having carried therein or thereon the said at least one cosmetic agent, whereby the said at least one cosmetic agent is deposited on the hair or skin when the composition is applied thereto.

DETAILED DESCRIPTION OF THE INVENTION AND PREFERRED EMBODIMENTS

Cosmetic Agent

Compositions in accordance with the present invention are advantageous for facilitating and/or enhancing deposition of any cosmetic agents for which difficulties in achieving efficient, cost-effective deposition have hitherto been encountered. The invention is particularly useful in respect of cosmetic agents which are water-insoluble, yet surfactant-solubilizable.

For the purpose of this invention, the cosmetic agent may be any material intended to be deposited onto the skin or the hair for imparting one or more cosmetic or other desirable benefits.

Suitable materials may include, but are not limited to, sunscreen materials, e.g. UV absorbers, after-sun treatment materials, occlusive oils, emollients, humectants, therapeutic and essential oils, perfumes, antiperspirants, moisturizers, color cosmetic materials, and even combinations of such agents, for example where a combination of cosmetic benefits is desired to be delivered by the composition. Further suitable cosmetic agents for use in the invention may include cosmetic oils, for example silicones, perfluoropolyether materials, hydrocarbons and glycerides, and the like.

A particularly useful application of the invention is for enhancing deposition of sunscreen materials onto hair from hair care compositions such as shampoos and conditioners.

Suitable sunscreens include benzophenone compounds, dibenzoyl methane derivatives and cinnamate derivatives, for example. A particularly preferred sunscreen is a UV absorber such as Parsol MCX (2-ethyl hexyl methoxy cinnamate) from GIVAUDAN Co Limited.

In the context of certain UV-absorbing sunscreen agents, for example, the use of sub-micron polymer latex particles as a carrier in accordance with the present invention may be able to give rise to a deposition system of higher weight for weight: efficiency compared with UV-absorbers which utilize polymerization of active monomers. The latter are also disadvantageous with regard to cost and the need for toxicity testing.

The level of cosmetic agent incorporated in the compositions of the invention may vary according to the type of cosmetic agent in question and the amount thereof which it is desired to deposit in a given application regime of the product. By way of example, a sunscreen material for instance may be present in the compositions in an amount of from about 0.1 to 5% by weight.

Polymer latex particles

The latex particles which act as the carrier for the cosmetic agent may be of any polymeric material which is a good film former and which is compatible with the cosmetic agent and any other components of the cosmetic composition.

As used herein, the term "polymer latex" means a stable colloidal dispersion of polymer particles in a liquid medium, preferably an aqueous or organic liquid phase. The polymer particles are kept suspended by the combined effects of their small particle size (less than about 1 micron), Brownian motion and the effect of surface charges. The latter are derived from the surface charges on the particles themselves and any surfactant which is used to stabilize the latex.

In order to be good film formers and substantive to hair or skin, polymers suitable for use in the present invention will generally have a relatively low glass transition temperature ($T_g$), a property which is not exhibited by the preferred polymers of the microparticles disclosed in EP-A-0306236. Typically, a glass transition temperature of the order of 30° C. is suitable, i.e. in the region of the temperature of normal use of the cosmetic compositions of the invention. By being good film formers, the polymers suitable for use in the present invention readily adhere to and form films on hair fibers and skin, thereby carrying down onto those substrates the cosmetic agent incorporated with the polymers in the cosmetic composition.

Suitable polymer latices for use in the present invention can be prepared using various polymerization techniques utilizing a wide range of monomers, the practical details of which are well known in the polymer art. Preferred is emulsion polymerization in an aqueous medium.

Suitable monomers for radical addition polymerization include those containing polymerisable olefinic unsaturation. Examples of such monomers include: styrene, butadiene, acrylonitrile, chloroprene, vinyl chloride, vinylidene chloride, isoprene, isobutylene, vinyl acetate, ethylene, propylene, butylene, vinyl pyrrolidone, and esters, e.g. methyl or other alkyl esters, of acrylic, methacrylic, vinyl acetic, maleic, crotonic and iraconic acids. Further suitable monomers include acrylic, methacrylic, itaconic, maleic, crotonic, para-styrene sulphonic, vinyl sulphonic, 2-methacryloyloxyethyl sulphonic and 2-acrylamido-2-methylpropyl sulphonic acids. The monomers may be used either singly or in combination.

Water-soluble monomers as listed above may desirably be used in minor proportions, e.g. from about 5 to about 20% by weight, with respect to a water insoluble monomer, such as a vinyl monomer. Alternatively, if such water-soluble monomers are used alone, then advantageously a cross-linking agent is also used.

Examples of polyfunctional monomers which may be used to effect cross-linking include divinylbenzene, divynyl ether, ethylene glycol dimethacrylate, pentaerthritol triacrylate and polyallyl sucrose.

Suitable initiators for polymerisation of the above monomers include redox systems, peroxides, perphosphates, percarbonates, persulphates, organic peroxyacids such as peracetic acid, and the persulphate/bisulphite/iron mixture. Examples of suitable radical. initiators include sodium or potassium persulphate, 2,2-azobis(amidinopropane) hydrochloride, dibenzoyl peroxide, 2,2-azobisisobutyronitrile (AIBN) and 4,4'-azobis(4-cyanovaleric acid). A water soluble initiator is preferable. Polymerisation temperature is preferentially in the range 40° to 90° C.

Suitable agents for effectlag chain transfer polymerisation include for example mercaptans, such as 1-dodecyl mercaptan or t-butyl mercaptan.

Suitable monomers for condensation polymerisation are those commonly used in interfacial polymerisation techniques, for example ethylene diamine, hexamethylene diamine, m/p-phenylene diamines, terephthaloyl chloride, isophthaloyl chloride, ethylene glycol and resorcinol.

Further suitable polymers for use in the present invention include natural and modified natural polymers, e.g. cellulose, modified cellulose, cellulose ethers and derivatives thereof, cellulose acetate, cellulose butyrate and hydroxyethyl cellulose.

Experimental techniques for carrying out appropriate polymerisation reactions are well known in the art and so will not be discussed further here.

The polymer latex particles forming the carrier for the cosmetic agent in the compositions of the present invention are of sub-micron particle size, i.e. less than about 1 micron. The particle size may be controlled by a variety of parameters, as is known in the polymer art. Primarily the particle size may be controlled by the type and concentration of any surfactant which is optionally used to stabilize the latex. Surfactant type can also determine the particle size distribution to some extent. The particle size may also be controlled by suitable choice of the polymerisation reaction conditions, especially stirring speed, reaction temperature and concentration of monomer(s) and/or initiator. Usually, fast reaction rates will produce smaller particles, whereas high monomer concentrations and low initiator levels favor bigger particles.

More preferably, the particle size of the polymer latex particles is in the range 0.01 to 1 micron, even more preferably 0.05 to 0.5 microns.

The sub-micron particle size of the latex particles of the compositions of the invention is important for giving the particles optimum surface area and thus optimum opportunity to act as a carrier for the cosmetic agent. It also gives the polymer particles good adhesion properties which are important for enabling the polymer particles to be retained, with the cosmetic agent, on the hair or skin onto which they are deposited. The very small particle size of the polymer latex particles is also useful for formulation compatability, less dulling of hair in hair treatment, and for achieving stable suspension of the particles in the cosmetic composition without the necessary use of thickeners or suspending agents,. as may be required for polymer particles having significantly larger particle sizes.

The polymer particles employed in the invention may be substantially solid or may be porous. It is however preferred, though not essential, that the particles have pores therein so that the cosmetic agent may be trapped within the particles and thus delivered to the intended site of application of the composition more effectively. Thus, not only can the polymer particles act as a delivery vehicle by having the cosmetic agent carried at the particle surface, but they may also act like microsponges and carry the cosmetic agent within the body of the particles.

Various techniques may be employed to obtain the polymer particles having the cosmetic agent trapped therein.

In the simplest technique, the cosmetic agent is introduced into the pores of the particles by simply mixing the two together, e.g. with stirring or other suitable physical means. More preferably, the cosmetic agent is introduced into the polymer particles during the polymerisation of the particle material itself.

For example, a preferred technique is to synthesize a polymer latex by aqueous emulsion polymerisation in the presence of the cosmetic agent. The cosmetic agent is therefore preferably soluble in the monomer and is incorporated in situ during the polymerisation process. The monomers used may include some polyfunctional monomer so as to produce a degree of cross-linking in the polymer structure, if that is desired.

In an alternative technique, a pre-formed crosslinked polymer latex is employed in the form of a suspension in water. The cosmetic agent is dissolved in an organic solvent, e.g. dichloromethane, toluene, which is able to swell the polymer particles. The solution is then brought into contact with the polymer latex, causing the polymer particles to swell. The cosmetic agent enters the swollen particles and subsequently the solvent is evaporated, leaving the cosmetic agent trapped in the latex particles.

In another technique, a linear polymer is converted into a latex in the presence of the cosmetic agent. This can be done by dissolving the polymer and the cosmetic agent in a low boiling point solvent, forming an emulsion of this in excess water and then removing the solvent.

As a general rule, therefore, for any of the procedures mentioned above, the polymer used in the invention should be capable of forming a stable colloidal dispersion in a liquid medium, e.g. an aqueous or aqueous-based medium.

While not intending to be bound by theory, it is believed that the above-described methods of incorporating the cosmetic agent in the polymer particles may give varying degrees of homogeneity of the cosmetic agent in the particles. For instance, incorporation by in situ polymerisation may be expected to give fairly homogeneous cosmetic agent-impregnated particles, whereas the microgel impregnation method may be expected to give particles having the cosmetic agent possibly more concentrated near the surface than towards the center of the particles. These properties may be important in selecting a suitable incorporation technique for a given cosmetic agent/polymer system, for example depending upon factors such as ease of incorporation of the cosmetic agent, retention and/or release characteristics of the polymer latex particles, concentration of cosmetic agent to be delivered to an intended site of deposition, etc.

The polymer latex particles, with the cosmetic agent trapped therein or simply carried thereon, may be incorporated into a final cosmetic composition by simple mixing with or without stirring with any remaining ingredients of the composition.

The type of polymer used to form the latex particles may if appropriate be selected in accordance with one or more other components which will be incorporated into the final cosmetic composition.

For example, when the cosmetic composition is in the form of a shampoo containing a surfactant which is principally an anionic surfactant, latex particles of a cationic polymer will be unsuitable. Since many cosmetic compositions may in practice contain one or more ionic components, it is therefore generally preferred that the latex particles are of a nonionic, or "neutral", polymeric material.

In the cosmetic compositions of the invention the polymeric latex particles acting as the carrier for the cosmetic agent may be present in an amount sufficient to give the required degree of enhanced deposition of the cosmetic agent to be deposited. Suitably, the polymer latex particles are present at a level of from about 0.1 to 70% by weight of the composition, more preferably from 1 to 40% by weight, even more preferably from 2 to 20% by weight.

Additional ingredients

The cosmetic compositions of the invention may contain, in addition to the cosmetic agent, polymer latex particles and preferably water, one or more additional components normally found in cosmetic compositions for the hair or the skin.

If desired or if necessary, the compositions may contain an effective amount of a suitable stabilizer to maintain the polymer particles stably dispersed throughout the composition matrix, though frequently this may not be necessary owing to the very small size of the latex particles. For this purpose one or more conventional suspending agents or emulsifiers may be used.

Suitable suspending agents are well known in the art and include for example polyacrylic acid, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), and heteropolysaccharide gums.

Polyacrylic acid is available commercially as Carbopol 420, Carbopol 488 or Carbopol 943 (ex Goodrich). Suitable polishers of acrylic acid cross-linked with a polyfunctional agent include those available commercially as Carbopol 910, Carbopol 934, Carbopol 940 and Carbopol 941 (ex Goodrich).

An example of a suitable copolymer of a carboxylic acid containing monomer and acrylic ester is Carbopol 1342 (ex Goodrich). Suitable examples of cross-linked polymers of acrylic acid and acrylate esters are Pemulan PR1 and Pemulan PR2. Suitable heteropolysaccharide gums include xanthan gum and guar gums.

A further class of suitable suspending agents are those materials which function as pearlescing agents in cosmetic compositions.

The pearlescing agent may be selected from a wide range of pearlescing agents, for example $C_{16}$–$C_{22}$ fatty acids, $C_{16}$–$C_{22}$ esters of fatty acids with alcohols and $C_{16}$–$C_{22}$ esters of fatty acids incorporating elements such as alkylene glycol unites and the like. Suitable alkylene glycol units include ethylene glycol and propylene glycol, though higher alkylene chain length glycols may also be employed. Suitable higher alkylene chain length glycols include polyethylene glycol and polypropylene glycol and the like. Preferably, the pearlescing agent is selected from polyethylene glycol mono- or diesters of $C_{16}$–$C_{22}$ fatty acids having from 1 to 7 ethylene oxide units.

The suspending agent may be present in the composition in an amount of from 1 to 60% by weight, preferably 2 to 40%, even more preferably 5 to 35%.

A further preferred additional ingredient in the cosmetic compositions in accordance with the invention is one or more surfactants, preferably selected from anionic, nonionic, amphoteric and zwitterionic surfactants.

Suitable anionic surfactants are the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene* sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauxyl phosphate, sodium lauryl ether sulphate 1EO, 2EO and 3EO, ammonium laury[sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other suitable nonionics include mono- or dialkyl alkanolamides. Examples include coco mono- or diethanolamide and coco mono-isopropanolamide.

Further suitable nonionic surfactants are the alkyl polyglycosides (APG's). Typically, the APG is one which comprises an alkyl group connected (optionally via a bridging group) to a block of one or more glycosyl groups. Preferred APG's are described by the following formula:

$$RO—(G)_n$$

wherein R is a branched or straight chain alkyl group which may be saturated or unsaturated and G is a saccharide group.

R may represent a mean alkyl chain length of from about $C_5$ to about $C_{20}$. Preferably, R represents a mean alkyl chain length of from about $C_8$ to about $C_{12}$. Most preferably the value of R lies between about 9.5 and about 10.5. G may be selected from $C_5$ or $C_6$ monosaccharide residues or mixtures of $C_5$ and $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; APG225, APG300, APG350, APG350 and APG600 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactant(s) may be present in the cosmetic compositions of the invention in an amount of from 1 to 70% by weight, preferably from 2 to 40% by weight.

Water is another preferred component of the compositions of the invention and may be present in an amount of from 1 to 99% by weight, preferably 20 to 80%, more preferably 40 to 75%.

Particularly when the cosmetic composition of the invention is in the form of a conditioning composition, e.g. for the hair, the composition preferably further comprises one or more conditioning agents. Suitable conditioning agents include:

cationic surfactants such as quaternary ammonium hydroxides, e.g. tetramethyl ammonium hydroxide, octyltrimethylammonium hydroxide, dodecyltrimethylammonium hydroxide, hexadecyltrimethylammonium hydroxide, cetyltrimethylammonium hydroxide, octyldimethylbenzylammonium hydroxide, decyldimethylbenzylammonium hydroxide, stearyldimethylbenzylammonium hydroxide, didodecyldimethyiammonium hydroxide, dioctadecyldimethylammonium hydroxide, tallow trimethylammonium hydroxide cocotrimethylammonium hydroxide, and the corresponding salts thereof e.g. chlorides, cetylpyridinium hydroxide and salts thereof e.g. chloride, Quaternium-5, Quaternium-31, Quaternium-18, and mixtures thereof;

silicone resins, for example oligomerous alkylpolysiloxanes, arylpolysiloxanes or alkylarylpolysiloxanes composed of suitable combinations of $R_3SiO_{0.5}$ units, $R_2SiO$ units, $RSiO_{1.5}$ units and $SiO_2$ units, their ratio being selected so that the resin has an average formula of $RnSiO_{[(4-n)/2]}$ where R is $C_{1-6}$ alkyl or aryl and n is from 0.7 to 1.8;

siloxane gums, such as high molecular weight alkylpolysiloxanes, arylpolysilcxanes or alkylarylpolysiloxanes having a viscosity greater than 100,000 cst, preferably greater than 500,000 cst, at volatile silicones, such as low molecular weight cyclic or linear polydimethylsiloxanes;

aminofunctional silicones, such as the amodimethicones and derivatives thereof;

quaternary silicones;

protein hydrolysates or quaternized protein hydrolysates;

cationic polymers, for example guar hydroxypropyl trimonium chloride, Quaternium -19, Quaternium -23, Quaternium -40, Quaternium -57, poly(dimethyldiallyammonium chloride), poly(dimethylbutenyl ammonium chloride)-α,ω-bis(triethanolanunonium chloride), poly(dipropyldia]lylanunonium chloride), poly(methyl-β-propaniodiallylammonium chloride), poly(diallylpiperidinium chloride), poly(vinyl pyridinium chloride), quaternized poly (vinyl alcohol), quaternized poly (dimethylaminoethylmethacrylate) and mixtures thereof.

The conditioning agent, if any, may be present in the cosmetic composition in a preferred amount of from 0.01 to 20% by weight of the total composition, more preferably 0.03 to 10%, especially 0.1 to 10%, typically 0.5 to 10% by weight.

The compositions of the invention may further include one or more deposition aids. Such materials are particularly preferred for enhancing the deposition and/or retention of the polymer latex particles carrying the cosmetic agent on the hair or the skin onto which the cosmetic composition is delivered.

An example of a suitable deposition polymer is a cationic derivative of guar gum.

Suitable cationic guar gum derivatives are those given the CTFA designation guar hydroxypropyl trimonium chloride, available commercially for example as JAGUAR C13S, which has a low degree of substitution of the cationic groups and a high viscosity. Other suitable materials include that known as JAGUAR C15, having a moderate degree of substitution and a low viscosity, JAGUAR C17 (high degree of substitution, high viscosity) and JAGUAR C16 which is a hydroxypropylated cationic guar derivative containing a low level of substituent groups as well as cationic quaternary ammonium groups. Also suitable is JAGUAR 162 which is a high transparency, medium viscosity guar having a low degree of substitution.

Compositions of the invention may further include one or more adjunct materials such as thickening agents, moisturizing agents, buffers, antibacterial agents, antidandruff agents, foam boosters, perfumes, dyes, coloring agents, preservatives, proteins, essential oils and herb and other plant extracts.

Use of the Cosmetic Compositions

The compositions of the invention may take any suitable form appropriate to the cosmetic agent(s) which they contain and are intended to deposit. Thus, preferred compositions in the form of body or hair shampoos may be applied to the skin or hair (especially wet hair), as appropriate, and worked to create a lather. The lather may be retained at the applied site for a short time, e.g. one or several minutes, before rinsing, or may be immediately rinsed. The procedure may be repeated if desired.

Retention of the latimer at the site of application and repetition of the application regime may be of additional benefit in enhancing even further the amount or rate of deposition of the cosmetic agent on the skin or hair. The invention is further illustrated by the following Examples. All amounts are in % by weight, unless otherwise stated.

EXAMPLE 1

The following shampoo composition was prepared by mixing the stated ingredients with stirring.

| Ingredient | Amount (% wt) |
| --- | --- |
| Sodium lauryl ether sulphate 2EO | 16 |
| Polymer latex (1) | 12 |
| Parsol MCX | 2 |
| Jaguar C13S | 0.3 |
| Preservative, perfume, colouring | qs |
| Water | to 100 |

(1) Polymer latex was a neutral aqueous latex (23.3% solids content) of 80:20 ethyl methacrylate/2-ethylhexyl acrylate copolymer, $T_g = +30°$ C., particle size approximately 0.06 microns, stabilized with 0.97% wt (based on latex) SLES 2EO.

In one embodiment, the latex was premixed with the Parsol MCX before adding to remaining ingredients. In an alternative embodiment, the Parsol MCX was dissolved in the mixture of monomers prior to initiation of the polymerization reaction, so that the sunscreen was incorporated into the polymer latex particles in situ.

EXAMPLE 2

A series of six experiments was conducted to demonstrate the superior deposition of a UV-absorbing sunscreen agent using the present invention as compared with direct incorporation (without the polymer latex carrier), and also to illustrate the use of an additional deposition agent, as is known in the art, to give even further enhanced efficacy of the deposition system of the invention.

Each of the following compositions was prepared by mixing, with stirring, the listed ingredients. All amounts are in weight %, unless otherwise stated.

| Ingredient | Example | | | | | |
|---|---|---|---|---|---|---|
| | A | B | C | D | E | F |
| Sodium lauryl ether sulphate 2EO | 16.00 | 16.00 | 16.00 | 16.00 | 16.00 | 16.00 |
| JAGUAR C13S | 0.30 | 0.10 | — | 0.30 | 0.10 | — |
| Polymer latex incorporating PARSOL MCX[1] | 18.00 | 18.00 | 18.00 | — | — | — |
| PARSOL MCX[2] | — | — | — | 1.08 | 1.08 | 1.08 |
| Formalin | 0.01 | 0.01 | 0.01 | — | — | 0.01 |
| Water | to 100 | to 100 | to 100 | to 100 | to 100 | to 100 |

[1] As used in Example 1, sunscreen incorporated in situ by polymerisation in presence of the sunscreen; latex contains 6 wt % PARSOL MCX
[2] Sunscreen incorporated directly, at same active level as in latex-incorporated Examples A to C An 8"/4 g switch of hair was wetted, treated with 0.25 g of shampoo and lathered for 30 seconds. The switch was then rinsed for 60 seconds and the procedure was repeated. The switch was then dried at 50° C. for 1 hour. PARSOL MCX was extracted from the switch using ethanol, by immersing the switch in ethanol for 1 hour, with agitation, removing the switch and making the resulting solution up to 100 ml with more ethanol. The amount of sunscreen deposited on the hair was determined by measurement of the concentration of the resultant ethanolic sunscreen solution by UV spectrophotometry.

The above procedure was carried out for each of the six shampoo compositions and the results are shown in the table below.

| Example | Weight of PARSOL MCX deposited/ mg per gram of hair |
|---|---|
| A | 0.191 |
| B | 0.177 |
| C | 0.141 |
| D | 0.074 |
| E | 0.084 |
| F | 0.056 |

A comparison of the results obtained with each of Shampoos A,B and C with the results obtained with each of shampoos D, E and F, respectively, clearly shows the superior level of deposition obtained by use of the present invention.

A comparison between the results obtained with each of shampoos A, B and C shows the additional enhancement of deposition of the sunscreen using a conventional deposition aid.

We claim:

1. A cosmetic composition for application to skin or hair and subsequent rinsing therefrom, comprising:
   (a) at least one sunscreen material,
   (b) as a carrier for said sunscreen material, latex particles of a polymer material having a particle size of less than about 1 micron;
   wherein said sunscreen material is carried in or on said polymer latex particles, for said polymer latex particles and sunscreen material to deposit jointly onto the hair or skin when the composition is applied thereto, whereby said polymer enhances the quantity of said sunscreen material retained on the hair or skin after rinsing of the composition therefrom.

2. A cosmetic composition according to claim 1, wherein the polymeric latex material has a particle size in the range 0.01 to 1 micron.

3. A cosmetic composition according to claim 1, wherein the polymer has a glass transition temperature in the region of the temperature of normal use of the cosmetic composition.

4. A cosmetic composition according to claim 1, wherein the polymer latex is formed by emulsion polymerisation in an aqueous medium.

5. A cosmetic composition according to claim 1, wherein the polymer is formed by radical addition polymerisation from one or more monomers having polymerisable olefinic unsaturation.

6. A cosmetic composition according to claim 1, wherein the polymer is cross-linked.

7. A cosmetic composition according to claim 1, further comprising at least one surfactant selected from anionic, nonionic, zwitterionic or amphoteric surfactants or mixtures thereof.

8. A cosmetic composition according to claim 1, further comprising a conditioning agent and/or a deposition aid for the cosmetic agent.

9. A cosmetic composition according to claim 1 which is a rinse-off composition for use on hair or skin.

10. A cosmetic composition according to claim 1 wherein said polymer latex particles are porous and have said sunscreen material trapped therein.

11. A method for depositing at least one sunscreen material onto skin or hair, comprising the steps of:
   (i) providing said sunscreen material in combination with a carrier therefore comprising latex particles of a polymer material having a particle size of less than about 1 micron and having said sunscreen material carried therein or thereon,
   (ii) applying said cosmetic composition to skin or hair,
   (iii) rinsing said cosmetic composition from said skin or hair,
   whereby said polymer latex particles and sunscreen material deposit jointly onto the skin or hair, and said polymer enhances the quantity of sunscreen material retained on the hair or skin after said rinsing.

12. A method according to claim 11 wherein the step (i) comprises forming said latex particles by polymerization in the presence of said sunscreen material, so as to trap sunscreen material in said latex particles.

13. A method according to claim 11 wherein the step (i) comprising mixing the polymer latex and the sunscreen material in the presence of a solvent which swells the latex particles, and subsequently removing said solvent to trap sunscreen material in said latex particles.

14. A method according to claim 11 wherein the step (i) comprises converting a polymer solution to a polymer latex in the presence of said sunscreen material, to trap sunscreen material in the polymer latex particles.

* * * * *